(12) United States Patent
Mori et al.

(10) Patent No.: US 7,745,135 B2
(45) Date of Patent: Jun. 29, 2010

(54) METHOD FOR DETECTING REACTION PRODUCT OF NUCLEIC ACID SYNTHESIS

(75) Inventors: Yasuyoshi Mori, Tochigi (JP); Kentaro Nagamine, Tochigi (JP)

(73) Assignee: Eiken Kagaku Kabushiki Kaisya (JP)

( * ) Notice: Subject to any disclaimer, the term of this patent is extended or adjusted under 35 U.S.C. 154(b) by 22 days.

(21) Appl. No.: 12/107,001

(22) Filed: Apr. 21, 2008

(65) Prior Publication Data

US 2009/0081664 A1    Mar. 26, 2009

Related U.S. Application Data

(62) Division of application No. 10/275,091, filed as application No. PCT/JP01/03572 on Apr. 25, 2001, now Pat. No. 7,374,879.

(30) Foreign Application Priority Data

May 1, 2000    (JP) .............................. 2000-132667

(51) Int. Cl.
*C12Q 1/68*    (2006.01)

(52) U.S. Cl. .................... 435/6; 435/91.1; 435/91.2; 536/24.33

(58) Field of Classification Search ................ None
See application file for complete search history.

(56) References Cited

U.S. PATENT DOCUMENTS 6,207,385 B1 *  3/2001  Stanley .......................... 435/6
6,258,568 B1    7/2001  Nyren

FOREIGN PATENT DOCUMENTS

| EP | 0 297 379 A2 | 6/1988 |
| EP | 0 663 447 A2 | 12/1994 |
| EP | 0707077 A2 | 9/1995 |
| EP | 0726312 A2 | 9/1995 |
| WO | WO 93/23564 | 11/1993 |
| WO | WO 97/22718 | 6/1997 |

OTHER PUBLICATIONS

Stratagene Catalog p. 39. 1988.*
Notomi et al. Nucleic Acids Research vol. 28:e63 i-vii. 2000.*
Cunningham et al. Biotechniques. vol. 9:713-714. 1990.
Davis et al. Biotechnol. Prog. vol. 13:747-756. 1997.
English Translation of International Preliminary Examination Report, Jun. 2002.
Gibson et al. Analytical Biochemistry vol. 254:18-22. 1997.
Mori et al., "Detection of Loop-Mediated Isothermal Amplification Reaction by Turbidity Derived from Magnesium Pyrophosphate Formation," Biochemical and Biophysical Research Communications 289:150-154 (2001).
Notomi et al. Nucleic Acids Research vol. 28 e63. 2000.

* cited by examiner

*Primary Examiner*—Heather G Calamita
(74) *Attorney, Agent, or Firm*—Fish & Richardson P.C.

(57) ABSTRACT

A method for detecting the occurrence of nucleic acid syntheses using an enzyme through the use of a generated insoluble substance as an indicator.

6 Claims, 10 Drawing Sheets

METHOD FOR DETECTING REACTION PRODUCT OF NUCLEIC ACID SYNTHESIS

CROSS-REFERENCE TO RELATED APPLICATIONS

This application is a divisional of U.S. application Ser. No. 10/275,091, filed on Nov. 1, 2002, which is a U.S. National Phase Application of International Application No. PCT/JP01/03572, filed on Apr. 25, 2001, claiming priority of Japanese Application Serial No. 2000-132667, filed on May 1, 2000. The disclosures of U.S. application Ser. No. 10/275,091, International Application No. PCT/JP01/03572, and Japanese Application Serial No. 2000-132667 are incorporated herein by reference in their entirety.

TECHNICAL FIELD

The present invention relates to a method for detecting the occurrence of nucleic acid amplification.

BACKGROUND ART

A method of analysis based on the complementarity of nucleic acid nucleotide sequence can be utilized to directly analyze genetic traits. Accordingly, this method of analysis is a very powerful means for identifying genetic diseases, canceration, microorganisms, etc. Further, because the gene itself is the object of detection, time-consuming and cumbersome procedures such as culture may be omitted.

However, since the detection of a target gene, which is present in a very small amount in a sample, is generally not easy, amplification of the target gene itself, its detection signal, or the like is required.

In the amplification of nucleic acids, the most general method for detecting the occurrence of amplification is carried out by subjecting the solution after amplification to agarose gel electrophoresis and binding a fluorescent intercalator such as ethidium bromide to the amplification product, thereby observing specific fluorescence. When there is no possibility of contamination by other DNA and only the occurrence of the amplification product is of interest, fluorescence can be observed by adding the fluorescent intercalator to the solution after amplification while omitting electrophoresis. While these methods are simple, a UV lamp and a darkroom are required to observe fluorescence.

Also, when amplification is performed using a primer or a nucleotide labeled with various label substances including a fluorescent dye, there is a method for detecting the label incorporated into the amplification product. This method, however, requires the separation of a free labeled primer (or nucleotide) that was not incorporated into the amplification product. Accordingly, this method is not suitable for the amplification of genes which uses very small amounts of reaction solution. Also, a labeled primer and nucleotide are expensive.

DISCLOSURE OF THE INVENTION

An object of the present invention is to provide a method for detecting the occurrence of nucleic acid amplification.

The present inventors have conducted concentrated studies in order to attain the above object. As a result, they found that use of an insoluble substance, which is generated by the nucleic acid amplification process itself, as an indicator enabled the detection of the occurrence of nucleic acid amplification in a simple manner with high sensitivity. This has led to the completion of the present invention.

More specifically, the present invention relates to a method for detecting the occurrence of nucleic acid syntheses using an enzyme through the use of a generated insoluble substance as an indicator. Further, the present invention relates to a method for detecting the occurrence of nucleic acid amplification by amplifying a target region on the polynucleotide chain and using an insoluble substance generated by the amplification as an indicator. The detection using the insoluble substance as an indicator can be carried out by measuring turbidity or by detecting precipitation. Measurement of turbidity or detection of precipitation can be carried out by adding a coagulant (e.g., polyacrylic acid or carboxymethyldextran).

The amplification methods include those carried out by the following steps:

(a) selecting a first arbitrary sequence F1c, a second arbitrary sequence F2c, and a third arbitrary sequence F3c in that order from the 3' terminus in a target region toward the 3' terminus on the polynucleotide chain, and a fourth arbitrary sequence R1, a fifth arbitrary sequence R2, and a sixth arbitrary sequence R3 in that order from the 5' terminus in the target region toward the 5' terminus of the nucleotide chain;

(b) preparing a primer containing sequence F2 which is complementary to F2c and, on the 5' side of F2, the same sequence as F1c; a primer containing sequence F3 which is complementary to F3c; a primer containing the same sequence as R2 and, on the 5' side of the sequence, sequence R1c which is complementary to R1; and a primer containing the same sequence as R3; and (c) synthesizing DNA in the presence of a strand displacement-type polymerase, the primers, a substrate, and a buffer using the nucleotide chain as a template. This method is referred to as the "Loop Mediated Isothermal Amplification (LAMP) method."

Also, amplification can be carried out by the LAMP method in accordance with an embodiment different from the above LAMP method by the following steps:

(a) selecting a first arbitrary sequence F1c and a second arbitrary sequence F2c in that order from the 3' terminus in a target region toward the 3' terminus on the polynucleotide chain and a third arbitrary sequence R1 and a fourth arbitrary sequence R2 in that order from the 5' terminus in the target region toward the 5' terminus on the nucleotide chain;

(b) preparing a primer containing sequence F2 which is complementary to F2c and, on the 5' side of F2, the same sequence as F1c; and a primer containing the same sequence as R2 and, on its 5' side, sequence R1c which is complementary to R1; and (c) synthesizing DNA in the presence of a strand displacement-type polymerase, the primers, a substrate, and a buffer using the nucleotide chain as a template for amplification.

Synthesis of DNA according to (c) above can be carried out in the presence of a melting temperature regulator (e.g., betaine, trimethylamine N-oxide, proline, dimethylsulfoxide, and formamide).

The present invention further relates to a method for monitoring nucleic acid amplification, wherein a target region on the polynucleotide chain is amplified and an insoluble substance generated by amplification is detected over time. Amplification can be carried out by, for example, the LAMP method described above.

Furthermore, the present invention relates to a kit for detecting the occurrence of nucleic acid amplification or for monitoring nucleic acid amplification comprising the following elements:

(a) when a first arbitrary sequence F1c, a second arbitrary sequence F2c, and a third arbitrary sequence F3c are selected in that order from the 3' terminus in the target region toward the 3' terminus on the polynucleotide chain and a fourth arbitrary sequence R1, a fifth arbitrary sequence R2, and a sixth arbitrary sequence R3 are selected in that order from the 5' terminus in the target region toward the 5' terminus of the nucleotide chain, a primer containing sequence F2 which is complementary to F2c and, on the 5' side of F2, the same sequence as F1c;

a primer containing sequence F3 which is complementary to F3c;

a primer containing the same sequence as R2 and, on the 5' side of the sequence, sequence R1c which is complementary to R1; and a primer containing the same sequence as R3;

(b) a polymerase catalyzing strand displacement-type synthesis of complementary chain;

(c) a nucleotide serving as a substrate for the element (b);

(d) a melting temperature regulator (e.g., betaine, trimethylamine N-oxide, proline, dimethylsulfoxide, and formamide); and (e) a coagulant (e.g., polyacrylic acid or carboxymethyl-dextran).

The present invention further relates to a kit for detecting the occurrence of nucleic acid amplification or for monitoring nucleic acid amplification comprising the following elements:

(a) when a first arbitrary sequence F1c and a second arbitrary sequence F2c are selected in that order from the 3' terminus in a target region toward the 3' terminus on the polynucleotide chain and a third arbitrary sequence R1 and a fourth arbitrary sequence R2 are selected in that order from the 5' terminus in the target region toward the 5' terminus of the nucleotide chain, a primer containing sequence F2 which is complementary to F2c and, on the 5' side of F2, the same sequence as F1c; and a primer containing the same sequence as R2 and, on the 5' side of the sequence, sequence R1c which is complementary to R1;

(b) a polymerase catalyzing strand displacement-type synthesis of complementary chain;

(c) a nucleotide serving as a substrate for the element (b);

(d) a melting temperature regulator (e.g., betaine, trimethylamine N-oxide, proline, dimethylsulfoxide, and formamide); and (e) a coagulant (e.g., polyacrylic acid or carboxymethyl-dextran).

Both the terms "same" and "complementary" used for characterizing the nucleotide sequence constituting the primer in the present invention do not mean being absolutely the same or absolutely complementary. That is, the same sequence is a certain sequence which includes sequences complementary to nucleotide sequences capable of annealing to a certain sequence. On the other hand, the complementary sequence means a sequence capable of annealing under stringent conditions to provide an origin of synthesis for complementary chains. In the present invention, the term "same" refers to homology of the nucleotide sequence of, for example, 90% or more, generally 95% or more, more preferably 98% or more. The term "complementary" refers to the same nucleotide sequence with a complementary sequence. Specifically, when homology of the nucleotide sequence to a complementary sequence is, for example, 90% or more, generally 95% or more, more preferably 98% or more, it can be said to be "complementary." Preferably, a complementary nucleotide sequence has at least one nucleotide completely congruous with the complementary sequence on its 3' terminus when it functions as an origin of synthesis for complementary chains.

The present invention will be described in detail below.

According to the present invention, a target region on the polynucleotide chain is synthesized or amplified, and the existence of an insoluble substance generated by synthesis or amplification is then detected, thereby associating the occurrence of nucleic acid amplification.

1. Target of Detection

The target of the detection according to the present invention includes all water-insoluble pyrophosphates. A pyrophosphoric acid is generated when a nucleotide is incorporated into a terminus of a nucleic acid chain. The terms "pyrophosphoric acid" and "pyrophosphate ion" are used as synonyms herein. Among substances forming an insoluble salt with pyrophosphoric acid, magnesium ion is an essential component for polymerase. Thus, magnesium pyrophosphate is suitable for this detection. When pyrophosphate other than magnesium pyrophosphate is the target of detection, some contrivance is required in a method for adding a substance for forming an insoluble salt with pyrophosphoric acid. More specifically, a substance, which has weak or no inhibition effect on polymerase, can be added prior to the amplification. Even though a substance strongly inhibits polymerase, it can also be added prior to amplification if the amount is small enough to the extent that it does not develop inhibitory effects. When a large amount of substance, which strongly inhibits polymerase, is intended to be added, similar detection can be carried out by adding the substance to the reaction solution after amplification. Targets of detection other than magnesium pyrophosphate include calcium pyrophosphate, barium pyrophosphate, and lead pyrophosphate.

The term "polynucleotide" in the present invention refers to a nucleic acid to be amplified, and generally includes DNA and RNA. The nucleic acid is generally included in a biological sample. The biological sample refers to animal, plant or microbial tissues, cells, cultures and excretions, or extracts therefrom. The biological sample includes intracellular parasitic genomic DNA or RNA such as virus or mycoplasma. The nucleic acid may be derived from nucleic acid contained in the biological sample. Examples thereof include cDNA synthesized from mRNA and nucleic acid amplified on the basis of nucleic acid derived from the biological sample.

2. Nucleic Acid Synthesis Using Enzyme

In the nucleic acid synthesis using an enzyme, pyrophosphoric acid is sometimes generated in the process of adding nucleotide to the terminus of nucleic acid with the aid of an enzyme. According to the present invention, the occurrence of nucleic acid amplification can be detected using pyrophosphoric acid generated upon such nucleic acid synthesis as an indicator.

The enzyme includes the following:

E. coli DNA polymerase;

Taq DNA polymerase;

T4 DNA polymerase;

Reverse Transcriptase;

SP6 RNA polymerase;

T7 RNA polymerase;

Terminal deoxynucleotidyl transferase;

Poly(A) polymerase;

Bst DNA polymerase; and

Vent DNA polymerase.

The reaction using each enzyme can be carried out under any conventional conditions (T. Maniatis et al., Molecular cloning, A Laboratory Manual, Second Edition, Cold Spring Harbor Laboratory Press, 1989).

3. Amplification

The insoluble substance to be detected in the present invention is pyrophosphate. Accordingly, amplification that can be employed in the present invention is not particularly limited as long as pyrophosphoric acid is generated by the incorporation of nucleotide into a nucleic acid chain. Also, polymerase is not particularly limited. For example, an amplification method referred to as the LAMP method, the Strand Displacement Amplification (SDA) method (for example, Japanese Patent Examined Publication (kokoku) No. 7-114718), and the Nucleic Acid Sequence Based Amplification (NASBA) method (Japanese Patent No. 2,650,159) can be employed in addition to the Polymerase Chain Reaction (PCR). Currently, PCR is the most general method as a technique of amplifying nucleic acid in vitro.

In the LAMP method, a loop structure is formed at a terminus of the nucleotide sequence to be amplified and, simultaneously with elongation by polymerase starting therefrom, a primer hybridized in a region within the loop dissolves the elongation product into a single-strand while elongating a nucleic acid chain by strand displacement. Since the generated single-strand nucleic acid has a self-complementary region at its terminus, it forms a loop at the terminus, and new elongation is initiated. The actual LAMP method proceeds under isothermal conditions and, thus, the reactions described above occur simultaneously and in parallel. The LAMP method is characterized by a very large amount of the amplification product in addition to a strand displacement-type reaction that proceeds under isothermal conditions. One of the reasons for this is that the LAMP method does not involve thermal denaturation, which deactivates polymerase. A large amount of the amplification product means that a large amount of pyrophosphoric acid, i.e., a large amount of insoluble substance, is generated. Accordingly, the LAMP method is suitable as a method for nucleic acid amplification to which the present invention is applied.

(1) LAMP Method

At the outset, a scheme of the LAMP method is shown (FIG. 1 and FIG. 2). In the LAMP method, a template polynucleotide, which is the target of amplification, is prepared. The template polynucleotide (DNA or RNA) can be prepared by chemical synthesis, or, in accordance with conventional methods from biological materials such as tissues or cells. In this case, the template polynucleotide is prepared so that suitable lengths of sequences (referred to as "bilateral sequences") are present on the sides (5' side and 3' side) in the target region for amplification (FIG. 1A). The term "bilateral sequences" refers to a sequence comprising a region from the 5' terminus in the target region to the 5' terminus of the polynucleotide chain and a sequence comprising a region from the 3' terminus in the target region to the 3' terminus of the polynucleotide chain (a portion indicated by two-headed arrows (← →) in FIG. 1A). The length of the bilateral sequences is 10 to 1,000 nucleotides, and preferably 30 to 500 nucleotides on the 5' side and the 3' side in the target region.

Predetermined regions are arbitrarily selected from the bilateral sequences in the template polynucleotide chain (FIG. 1A) containing the target region and the bilateral sequences. Specifically, a first arbitrary sequence F1c, a second arbitrary sequence F2c, and a third arbitrary sequence F3c are selected in that order from the 3' terminus in the target region toward the 3' terminus of the polynucleotide chain (FIG. 1B). Similarly, a fourth arbitrary sequence R1, a fifth arbitrary sequence R2, and a sixth arbitrary sequence R3 are selected in that order from the 5' terminus in the target region toward the 5' terminus of the polynucleotide sequence (FIG. 1B). When selecting the arbitrary sequence F1c and the arbitrary sequence R1, the distance between F1c and R1 can be 0 nucleotide, i.e., to be contiguous. Alternatively, it can be selected in such a manner that F1c and R1 are allowed to partially overlap. The first to the sixth regions are respectively and arbitrarily selected in accordance with the sequences of prepared polynucleotide chains. Each region to be selected comprises preferably 5 to 100 nucleotides, and more preferably 10 to 50 nucleotides. Selection of the nucleotide length facilitates annealing of the primer described below.

Each of the arbitrary sequences is preferably selected so that, instead of intermolecular annealing, the amplification product obtained by the LAMP method preferentially initiates the intramolecular annealing between sequence F1c and sequence F1 and between sequence R1 and sequence R1c as shown in FIG. 2L, and forms a terminal loop structure. For example, in order to preferentially initiate the intramolecular annealing, it is important to consider the distance between sequence F1c and sequence F2c and the distance between sequence R1 and sequence R1c when selecting the arbitrary sequences. More specifically, both sequences are preferably located within a distance of 0 to 500 nucleotides, preferably 0 to 100 nucleotides, and most preferably 10 to 70 nucleotides. Numerical values respectively represent the number of nucleotides without containing sequences F1c and F2c and sequences R1 and R2.

Subsequently, a primer referred to as the "FA primer" is designed and synthesized, and this is annealed to F2c. The term "FA primer" includes sequence F2 that is complementary to region F2c and another sequence which is the same as F1c (this may be referred to as "F1c" for convenience). Examples thereof include those having a structure in which the 3'-terminus of sequence F1c is linked to the 5' side of F2 (FIG. 1C). The term "annealing" refers to the formation of a double-strand structure of a nucleotide chain through nucleotide pairing based on the Watson-Crick model. After the FA primer is annealed to sequence F2c on the template polynucleotide chain, synthesis of DNA strand is initiated starting from F2 in the FA primer (FIG. 1D). Subsequently, a primer containing sequence F3 which is complementary to F3c (hereinafter this may be referred to as "F3 primer") is annealed to sequence F3c on the template polynucleotide chain (FIG. 1D). Strand displacement-type synthesis of DNA is then carried out starting from the annealed F3 primer (FIG. 1E). When a double-strand structure, which has been produced through the hybridization of a polynucleotide to a template for the synthesis of a complementary chain, is subjected to a reaction which synthesizes, starting from a primer, a complementary chain while separating the polynucleotide from the template, this process is termed as "strand displacement-type synthesis of DNA." Specific examples thereof include a reaction in which synthesis proceeds so as to displace the chain synthesized by the FA primer with the chain synthesized by the F3 primer. In other words, the complementary chain of the template polynucleotide chain synthesized by the FA primer can be displaced by a chain elongated from the F3 primer in such a manner that the complementary chain is separated.

Two types of nucleotide chains, the following (i) and (ii), can be obtained by the above-described synthesis.

(i) A nucleotide chain containing sequence "(5')F3-F2-F1-target region-R1c-R2c-R3c(3')" which is complementary to sequence "(3')F3c-F2c-F1c-target region-R1-R2-R3(5')" in the template polynucleotide chain (FIG. 1F).

(ii) A nucleotide chain formed into a single-strand by displacement (separated), i.e., a nucleotide chain containing "(5')F1c-F2-F1-target region-R1c-R2c-R3c(3')" having the same sequence as F1c on its 5' terminal side (FIG. 1G).

F1 and F1c are complementary to each other in the nucleotide chain according to (ii) above and, thus, they hybridize with each other based on the intrachain hydrogen bond between F1 and F1c, thereby forming a hairpin loop (FIG. 1G). F2 is contained in the hairpin loop.

Subsequently, a primer referred to as the "RA primer" is annealed to sequence R2c in the nucleotide chain according to (ii) above. In the RA primer the 3' side of sequence R1c complementary to sequence R1 is linked to the 5' side of sequence R2. Synthesis of DNA strand is then initiated starting from the RA primer (FIG. 1H). When the elongated DNA synthesized starting from the RA primer reached the end of the double-strand chain formed between F1 and F1c, the sequence of F1c is displaced with the elongated DNA in the same manner as the displacement shown in FIG. 1E (FIG. 1I). A primer containing sequence R3 which is complementary to sequence R3c (hereinafter it may be referred to as "R3 primer") is then annealed to R3c of the template polynucleotide chain (FIG. 1I). Strand displacement-type synthesis of DNA is then carried out starting from the annealed R3 primer (FIG. 2J). Two types of nucleotide chains, i.e., the following (iii) and (iv), are synthesized based on the above synthesis.

(iii) A nucleotide chain "(3')F1-F2c-F1c-target region-R1-R2-R3(5')" which is complementary to sequence "(5')F1c-F2-F1-target region-R1c-R2c-R3c(3')" (FIG. 2K).

(iv) A nucleotide chain "(3')F1-F2c-F1-target region-R1-R2-R1c(3')" having F1 located closest to the 3' terminal side, and R1c located closest to the 5' terminal side (FIG. 2L).

The sequence according to (iv) above forms a hairpin loop by the intrachain hydrogen bond between sequences F1 and F1c existing on the 3' side and between sequences R1 and R1c on the 5' side (FIG. 2L).

Subsequently, among the nucleotide chains according to (iv) above, region F2 of the FA primer is annealed to F2c in the hairpin loop portion on the 3' side (FIG. 2M). Synthesis of DNA strand is initiated starting from F1 annealed by the intrachain hydrogen bond. In FIG. 1M, the elongation chain synthesized starting from F1 reaches the 5' terminus by opening the hairpin loop formed by R1-R2-R1c. In contrast, when a reaction proceeds starting from F2, a chain, which is complementary to a chain constituted by "F1c-target region-R1-R2-R1c," is synthesized. In this case, F1 and the chain "F1-target region-R1c-R2c-R1" synthesized starting from F1 are displaced by the chain which is synthesized starting from F2. This provides for double-strand DNA having a single-strand protrusive construction "-target sequence-R1c-R2c-R1." The portion having a single-strand protrusive construction forms a hairpin loop by forming the intrachain hydrogen bond between R1c and R1 of a portion having a single-strand protrusive construction ("R1c-R2c-R1") (FIG. 2N). This construct initiates synthesis of DNA strand starting from R1 annealed by the intrachain hydrogen bond (FIG. 2N). Two types of nucleotide sequences, the following (v) and (vi), are obtained based on the above synthesis.

(v) Sequence "(3')R1-R2-R1c-target region-F1-F2-F1c-target region-R1-R2c-R1c-target region-F1-F2c-F1c-target region-R1-R2-R1c(5')" (FIG. 2O).

(vi) A sequence having F1c located closest to the 3' terminal side and R1 located closest to the 5' terminal side "(3') F1c-F2-F1-target region-R1c-R2c-R1(3')" (FIG. 2P).

The nucleotide chains according to (v) and (vi) above respectively form a hairpin loop having R2c as a loop portion and a hairpin loop having F2 and R2c as another loop portion by intrachain hydrogen bond. The RA primer is annealed to the portion R2c forming the hairpin loop in two sequences, i.e., (v) and (vi) above, synthesis of DNA starting from the primer is initiated, and synthesis of nucleotides chain (complementary chain with sequence shown in (vi)) containing a target sequence proceeds. This complementary chain is the same as the sequence shown in FIG. 2L and, thus, the reactions according to FIGS. 2L to P are thereafter repeated. In contrast, the reaction from FIG. 1A can proceed and, thus, amplification of polynucleotide chain proceeds by repeating this series of syntheses.

The above-described amplification is carried out using four types of primers, i.e., the FA primer, the RA primer, the F3 primer, and the R3 primer. Alternatively, amplification under isothermal conditions can be initiated by using only two types of primers, the FA primer and the RA primer, without using the F3 primer and the R3 primer. In this alternative amplification, a melting temperature (Tm) regulator, for example, betaine, trimethylamine N-oxide (TMANO), proline, dimethylsulfoxide (DMSO), or formamide preferably is present in the reaction system.

(2) Reaction Condition

In the reaction in accordance with the LAMP method, the following ingredients are added to a template single-strand nucleic acid, stable nucleotide pairing between a nucleotide sequence constituting FA or RA and a complementary nucleotide sequence thereof can be formed in a buffer, and the reaction proceeds through incubation at a temperature capable of maintaining enzyme activity. The incubation temperature is 50 to 75° C. and preferably 55 to 70° C., and the incubation time is 1 minute to 10 hours and preferably 5 minutes to 4 hours.

(i) Four types of oligonucleotides (FA, RA, outer primer F3, and outer primer R3)

(ii) Strand displacement-type synthesis of complementary chain by DNA polymerase (iii) A nucleotide serving as a substrate for DNA polymerase In the LAMP method according to the above two embodiments, the FA primer and the RA primer are also referred to as "inner primers" and the F3 primer and the R3 primer are also referred to as "outer primers."

Synthesis of nucleotide chain from the outer primer should be initiated after synthesis of nucleotide chain from the inner primer. A method for satisfying this condition includes the one which sets the concentration of the inner primer higher than that of the outer primer. More specifically, the concentration of the inner primer can be set higher than that of the outer primer by 2- to 50-fold, preferably 4- to 25-fold.

Polymerase, which catalyzes the strand displacement-type synthesis of complementary chain (this may be referred to as "strand displacement-type polymerase), includes Bst DNA polymerase, Bca(exo-) DNA polymerase, the Klenow fragment of E. coli DNA polymerase I, Vent DNA polymerase, Vent(Exo-) DNA polymerase (exonuclease activity is removed from Vent DNA polymerase), DeepVent DNA polymerase, DeepVent(Exo-) DNA polymerase (exonuclease activity is removed from DeepVent DNA polymerase), φ29 phage DNA polymerase, MS-2 phage DNA polymerase, Z-Taq DNA polymerase (Takara Shuzo Co., Ltd.), and KOD DNA polymerase (Toyobo Co., Ltd.).

This reaction is conducted in the presence of, for example, a buffer giving suitable pH to the enzyme reaction, salts necessary for maintaining the catalytic activity of the enzyme or for annealing, a protective agent for the enzyme, and, if necessary, a regulator for melting temperature (Tm). A buffer, such as Tris-HCl having a buffering action in the range of weakly alkaline to neutral, is used. The pH is adjusted depending on the DNA polymerase being used. As salts, $MgCl_2$, KCl, NaCl, $(NH_4)SO_4$ etc. are suitably added to maintain the activity of the enzyme and to regulate the melting temperature (Tm) of the nucleic acid. Bovine serum albumin or sugars can be used as a protective agent for enzyme. Further, betaine (N,N,N-trimethylglycine), trimethylamine N-oxide (TMANO), proline, dimethyl sulfoxide (DMSO), or formamide is used as a regulator for melting temperature (Tm). By the use of the regulator for melting temperature (Tm), annealing of the oligonucleotide can be regulated under restricted temperature conditions. In particular, betaine and trimethylamine N-oxide (TMANO) are also effective for improving the efficiency of strand displacement by virtue of its isostabilization properties. By adding betaine in an amount of 0.2 to 3.0 M, preferably about 0.5 to 1.5 M to the reaction solution, its promoting action on the nucleic acid amplification of the present invention can be expected. Because these regulators for melting temperature act for lowering melting temperature, conditions giving suitable stringency and reactivity have to be empirically determined in consideration of other reaction conditions such as concentration of salts and reaction temperature.

4. Detection

In the method for detecting the occurrence of nucleic acid amplification according to the present invention, an insoluble substance in the reaction product is used as an indicator for detection. Further, detection of the insoluble substance generated by the amplification over time enables monitoring of nucleic acid amplification. The insoluble substance to be detected is pyrophosphate that is generated by binding between pyropliosphoric acid generated from the nucleotide, which was used in amplification, and a metal ion in the reaction solution, for example, magnesium pyrophosphate.

(1) Visual Detection

The simplest method for detecting this insoluble substance generated by the amplification is carried out by visually inspecting the turbidity of the reaction solution after amplification. The second simplest method is carried out by subjecting the reaction solution after amplification to centrifugation and visually inspecting for precipitated insoluble substances.

(2) Detection of Turbidity

The absorbance or scattered light intensity of the reaction product is measured to determine the turbidity of the reaction solution. The obtained turbidity can be used as an indicator to detect nucleic acid amplification. When measuring the absorbance, commonly employed measuring apparatus can be used. The wavelength for measuring the absorbance can be suitably determined, and measurement is generally carried out at 300 to 800 nm, preferably at the dominant wavelength of 340 to 400 nm, and at the complementary wavelength of 600 to 800 nm. When measuring the scattered light intensity, commonly employed measuring apparatus can be used.

According to the present invention, in particular, measurement of changes in the absorbance over time enables the monitoring of the progress on nucleic acid amplification depending on the duration of the reaction time.

(3) Detection Using Filter

The reaction product can be filtered through a colored filter, and the residue on the filter can be detected visually or based on changes in light reflectance.

Addition of a coagulant such as polyacrylic acid or carboxymethyldextran increases the precipitate yield and can improve the detection sensitivity Further, these insoluble substances can be colored or labeled, thereby facilitating the detection or improving the detection sensitivity. For example, addition of Acid Orange colorizes the insoluble substances and, thus, detection is facilitated.

5. Kit for Detecting Occurrence of Nucleic Acid Amplification or for Monitoring Nucleic Acid Amplification In the method for detecting the occurrence of nucleic acid amplification or the method for monitoring nucleic acid amplification according to 4 above, reagents necessary for implementation can be packaged and supplied as a kit. The specific examples include a kit comprising the following elements.

[Element of Kit]

(a) When a first arbitrary sequence F1c, a second arbitrary sequence F2c, and a third arbitrary sequence F3c are selected in that order from the 3' terminus in the target region toward the 3' terminus of the polynucleotide chain and a fourth arbitrary sequence R1, a fifth arbitrary sequence R2, and a sixth arbitrary sequence R3 are selected in that order from the 5' terminus in the target region toward the 5' terminus of the polynucleotide chain, a primer containing sequence F2 which is complementary to F2c and, on the 5' side of F2, the same sequence as F1c;

a primer containing sequence F3 which is complementary to F3c;

a primer containing the same sequence as R2 and, on the 5' side of the sequence, sequence R1c which is complementary to R1; and a primer containing the same sequence as R3;

(b) a polymerase catalyzing strand displacement-type synthesis of complementary chain;

(c) a nucleotide serving as a substrate for the element (b); and (d) a coagulant (e.g., polyacrylic acid or carboxymethyldextran).

The elements of the kit can vary according to the embodiment of the LAMP method to be employed. Specifically, a primer containing the sequence F3 which is complementary to arbitrary sequence F3c and a primer containing the same sequence as arbitrary sequence R3 can be optionally omitted from the element (a). Preferably, a melting temperature regulator (for example, betaine, trimethylamine N-oxide, proline, dimethylsulfoxide, or formamide) is added as a element. Further, a buffer giving suitable conditions to the enzyme reaction and reagents necessary for detecting the reaction product of synthesis can be optionally added. According to a preferred embodiment of the present invention, reagents necessary for one reaction can be supplied in the state of being fractionated into reaction vessels.

BEST MODE FOR CARRYING OUT THE INVENTION

The present invention will be described in more detail with reference to the following examples, however, the technical scope of the present invention is not limited to these examples.

EXAMPLE 1

(1) LAMP Reaction

| Composition of reaction solution (in 100 μL) |
| --- |
| 20 mM Tris-HCl pH 8.8 |
| 10 mM KCl |
| 10 mM $(NH_4)_2SO_4$ |
| 4 mM $MgSO_4$ |
| 1 M betaine |
| 0.4 mM dNTP |
| 8 U Bst DNA polymerase |

Non-denatured $1 \times 10^4$ molecules λDNA (SEQ ID NO: 1) was used as a polynucleotide to be amplified.

```
                                        (SEQ ID NO: 1)
5'-GCTTATCTTTCCCTTTATTTTTGCTGCGGTAAGTCGCATAAAACCA

TTCTTCATAATTCAATCCATTTACTATGTTATGTTCTGAGGGGAGTGAAA

ATTCCCCTAATTCGATGAAGATTCTTGCTCAATTGTTATCAGCTATGCGC

CGACCAGAACACCTTGCCGATCAGC-3'
```

Regions corresponding to a target region, F1c, F2c, F3c, R1, R2, and R3 in SEQ ID NO: 1 are as follows.

Target region: "G" only, the position 92 in the nucleotide sequence shown in SEQ ID NO: 1

F1c: Positions 68 to 91 in the nucleotide sequence shown in SEQ ID NO: 1 (24 bp)

F2c: Positions 25 to 50 in the nucleotide sequence shown in SEQ ID NO: 1 (26 bp)

F3c: Positions 1 to 24 in the nucleotide sequence shown in SEQ ID NO: 1 (24 bp)

R1: Positions 93 to 115 in the nucleotide sequence shown in SEQ ID NO: 1 (23 bp)

R2: Positions 129 to 152 in the nucleotide sequence shown in SEQ ID NO: 1 (24 bp)

R3: Positions 153 to 172 in the nucleotide sequence shown in SEQ ID NO: 1 (20 bp)

Primers having the following sequences were put into the reaction solution and allowed to react at 65° C. for 1 hour.

Primers:

```
1600 nM inner primer FA
                                        (SEQ ID NO: 2)
5'-TCCCCTCAGAACATAACATAGTAATGCGGTAAGTCGCATAAAAACCA

TTC-3'

1600 nM inner primer RA
                                        (SEQ ID NO: 3)
5'-TGAAAATTCCCCTAATTCGATGAGGTCGGCGCATAGCTGATAACAA

T-3'

400 nM outer primer F3
                                        (SEQ ID NO: 4)
5'-GCTTATCTTTCCCTTTATTTTTGC-3'

400 nM outer primer P3
                                        (SEQ ID NO: 5)
5'-GCTGATCGGCAAGGTGITCT-3'
```

(2) White Precipitate by LAMP

Figure 1:
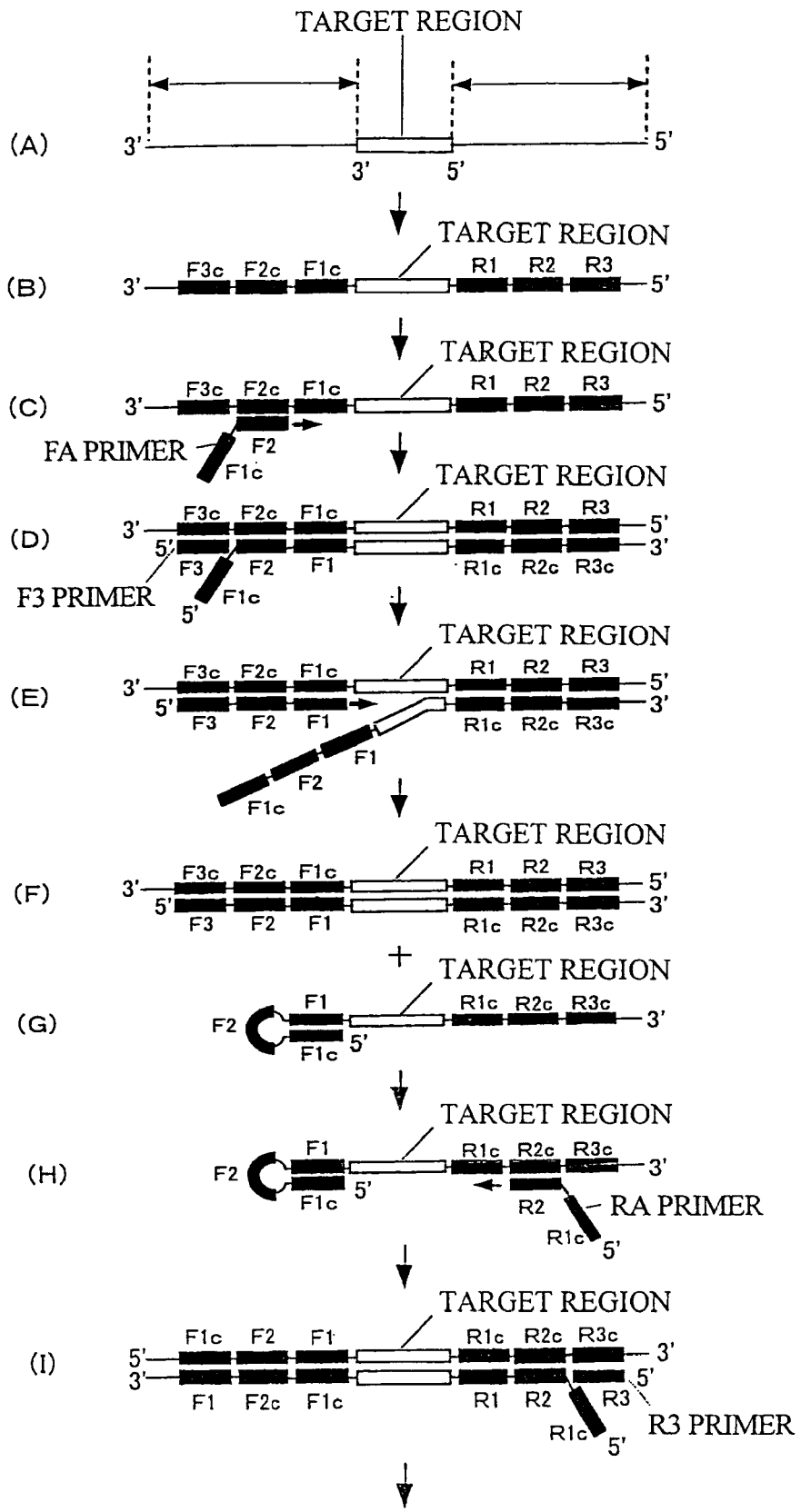
FIG. 1 shows a scheme of amplification by the LAMP method.
Figure 2:
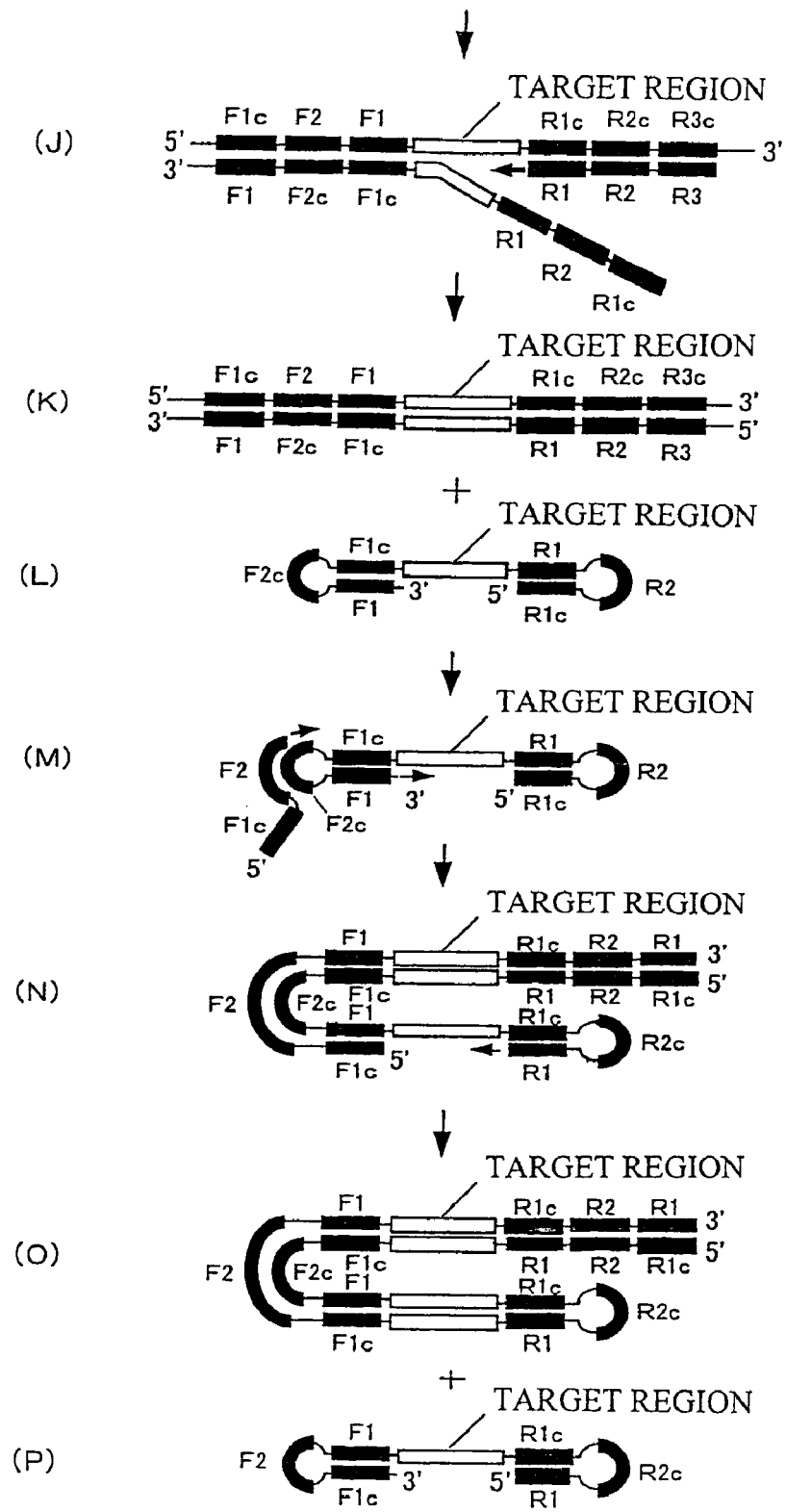
FIG. 2 shows a scheme of amplification by the LAMP method.
Figure 3:
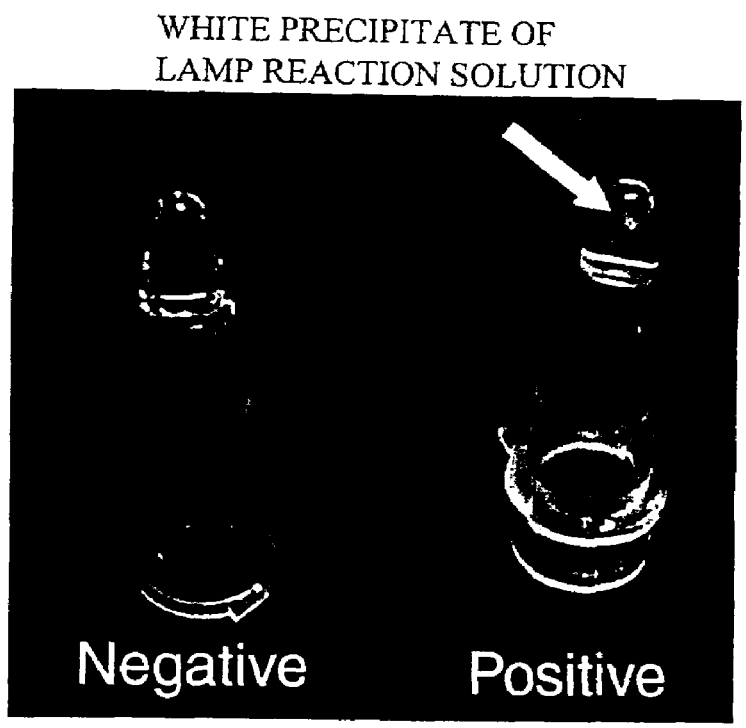
FIG. 3 is a photograph showing a white precipitate of the product obtained by amplification by the LAMP method.

After the completion of the LAMP reaction, centrifugation was conducted at 10,000 rpm for 5 minutes. After centrifugation, a white precipitate was detected at the bottom of the tube (0.2 μl tube) (at right in FIG. 3). The tube at left in FIG. 3 is a negative control (without template).

(3) Measurement of Absorbance of LAMP Reaction Product

Measuring apparatus: Ultrospec 2000, Pharmacia Biotech Ltd.

Optical path length: 1 cm

Cell capacity: 100 μl

After the completion of the LAMP reaction, the absorbance at 500 nm was measured. While the sample of the preceding reaction exhibited an absorbance of 1.21, the sample with failure in reaction (a negative control) exhibited that of 0.25.

Figure 4:
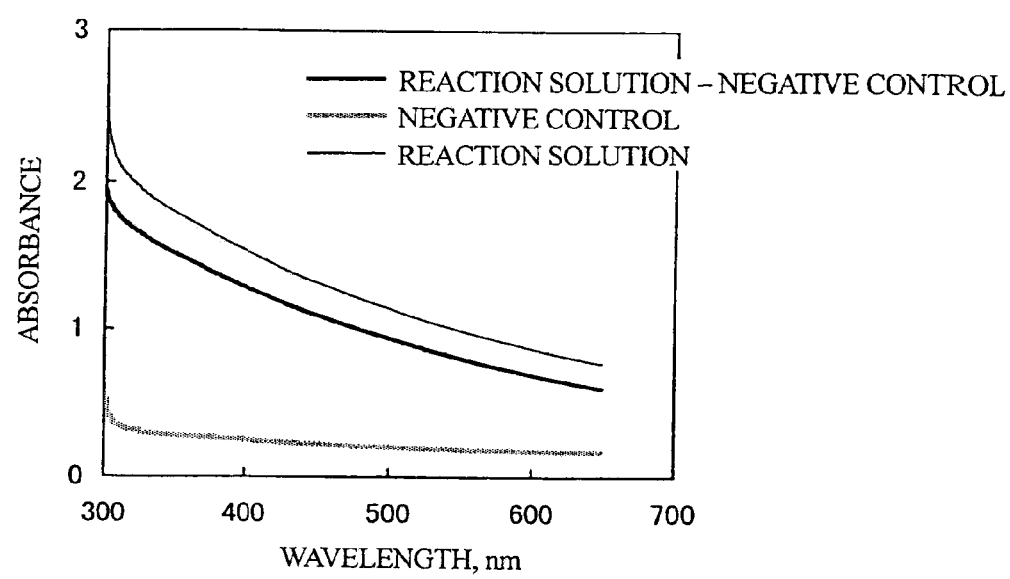
FIG. 4 is a diagram showing the absorption spectrum of the LAMP reaction solution.

As a result of the measurement of the absorption spectrum using a 1 cm cell at room temperature, the LAMP reaction solution exhibited a broad absorption spectrum from 300 nm to 600 nm (FIG. 4).

Because dNTPs or DNA does not have absorption in such a long-wavelength region, this broad absorption is deduced to be based on the scattering of the incident light by fine particles in the reaction solution. The reaction solution was analyzed using a light-scattering particle analyzer in order to confirm the above deduction. As a result, the formation of fine particles having an average diameter of about 2 μm was confirmed.

Thus, the occurrence of nucleic acid amplification by the LAMP reaction was found to be confirmable using absorbance (turbidity) as an indicator.

EXAMPLE 2

Analysis of Precipitate

A white precipitate obtained by the LAMP method was presumed to be magnesium pyrophosphate, and whether it was pyrophosphate or not was first examined. 100 μl of 1N NaOH was added to the precipitate obtained in Example 1, and the mixture was incubated at 65° C. for 5 minutes. After centrifugation, the supernatant was transferred to another tube, and 100 μl of 1N HCl was added thereto in order to neutralize the solution. Upon addition of 0.1N $AgNO_3$ to the solution, the mixture whitened (generation of $Ag_4P_2O_7$). This indicated that the substance was pyrophosphate.

Subsequently, whether or not the metal was magnesium was examined using a titan yellow reagent The titan yellow reagent is for detecting magnesium or boron. The reaction system in question, however, does not contain boron, thus a positive result would mean the presence of magnesium only.

After 20 μl of 0.1N HCl was added and dissolved in the precipitate, 1 μl of 2 mg/ml titan yellow reagent was added. 20 μl of 1N NaOH was added in order to alkalinize the solution. As a result, a precipitate, which exhibited a color of reddish brown by the titan yellow reagent, was observed. This demonstrated that the existence of magnesium in the white precipitate.

Figure 5:
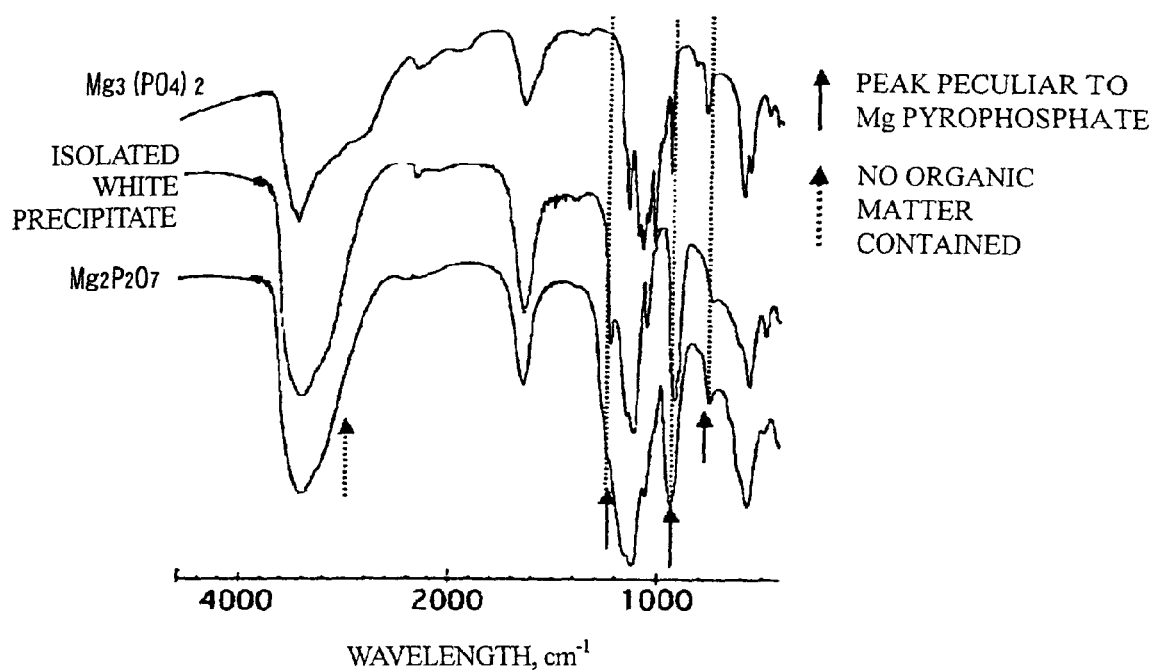
FIG. 5 is a diagram showing the infrared absorption spectra of a white precipitate and commercially available $Mg_3(PO_4)_2$ and $Mg_2P_2O_7$.

The precipitate was subjected to IR spectrum analysis. Specifically, the precipitate obtained in Example 1 was coagulated by centrifugation. The coagulated product was washed three times with water, and it was then dried in a silica gel desiccator for 1 week. The obtained dry substance was subjected to IR spectrum measurement by the KBr method at room temperature acquisition time; 64 times/measurement. Commercially available magnesium pyrophosphate ($Mg_2P_2O_7$) and magnesium monophosphate ($Mg_3(PO_4)_2$) (manufactured by Merck) were used as controls. As a result, the IR spectrum of the precipitate was congruous with commercially available $Mg_2P_2O_7$ as shown in FIG. 5. Since no CH stretching peak (2,900 $cm^{-1}$ in general; around the dash-lined arrow in FIG. 5), which is peculiar to an organic compound, was observed, it was concluded that the precipitate contained substantially no organic matter.

This result demonstrated that the white precipitate was magnesium pyrophosphate.

EXAMPLE 3

Generation of Precipitate by Magnesium Ion and Pyrophosphate Ion $K_4P_2O_7$ was added to the following reaction solution to bring the concentration to a desired level, and the mixture was allowed to react at 65° C. for 1 hour. The precipitate generated thereupon was inspected by measuring the absorbance of the reaction solution (A 440 nm).

| Composition of reaction solution |
| --- |
| 20 mM Tris-HCl pH 8.8 |
| 10 mM KCl |
| 10 mM $(NH_4)_2SO_4$ |
| 4 mM $MgSO_4$ |

Figure 6:
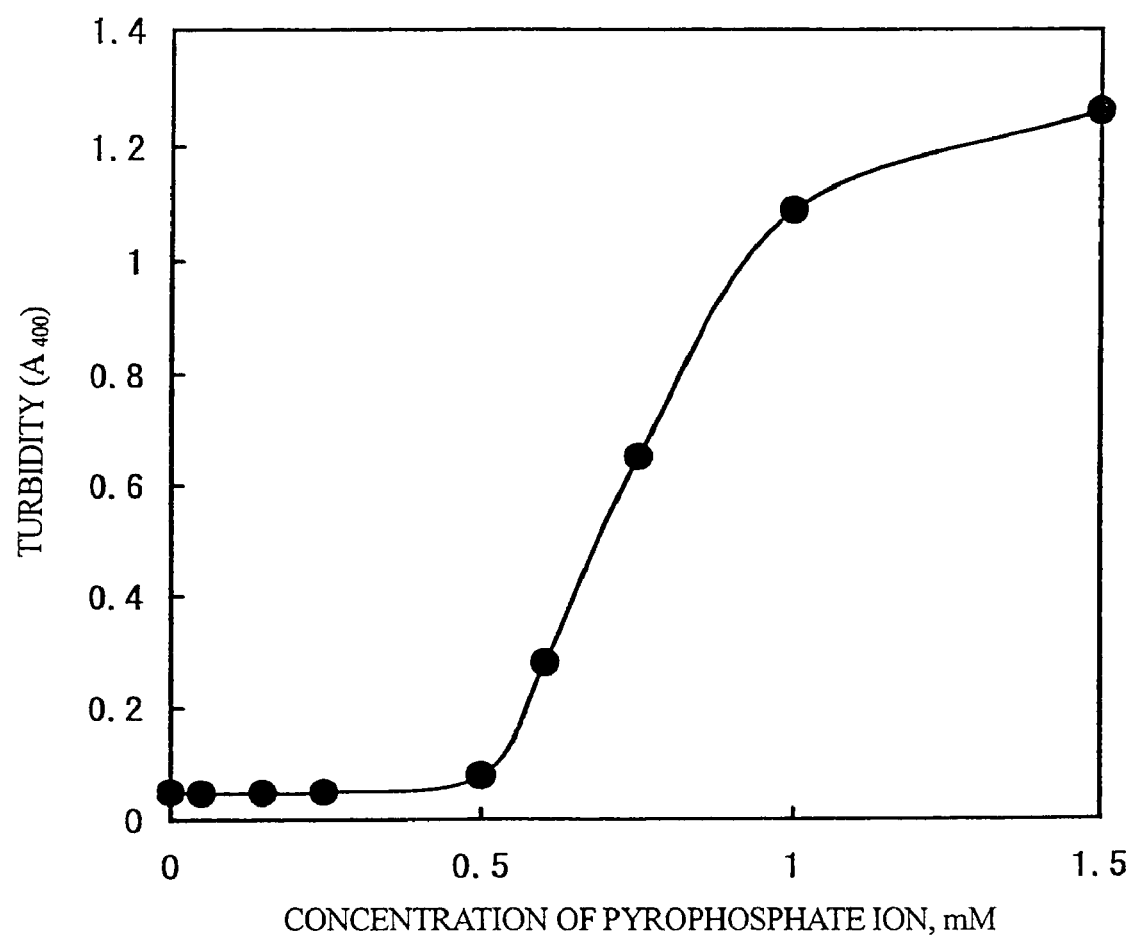
FIG. 6 is a diagram showing a correlation between the turbidity and the concentration of pyrophosphate ion at the wavelength of 400 nm.

The result was shown in FIG. 6. As shown in FIG. 6, a precipitate was generated when the concentration of $P_2O_7$ ion exceeded 0.5 mM. In order to generate 0.5 mM or more $P_2O_7$ ion, 4 μg/25 μl or more DNA should be synthesized. In general, 20 μg/25 μl or more DNA can be synthesized by LAMP. In contrast, the amount of DNA synthesized by PCR is about 1/100 of that synthesized by LAMP and, thus, the precipitate of magnesium pyrophosphate is not generated by general PCR. When an amplification method such as LAMP, which can synthesize a large amount of DNA, is invented in the future, this method is useful for detecting the occurrence of amplification.

EXAMPLE 4

Change in Absorbance by LAMP Reaction Over Time (Monitoring)

Figure 7:
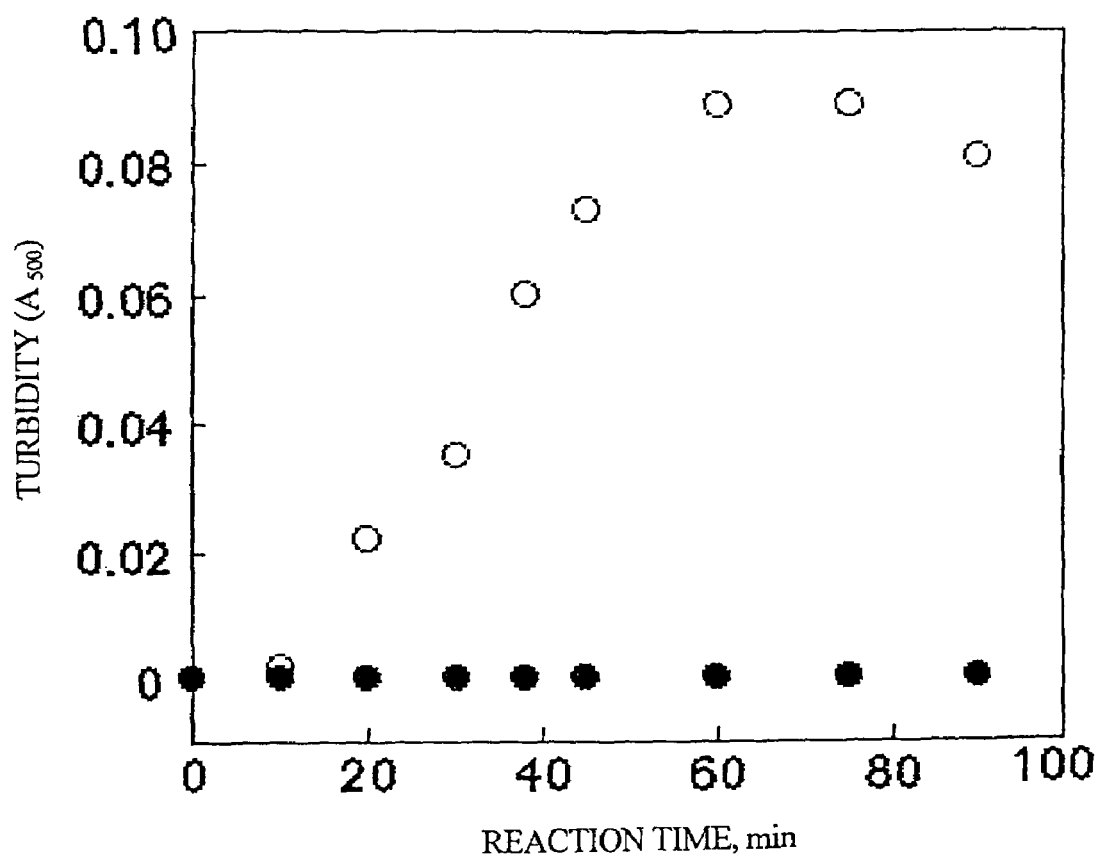
FIG. 7 is a diagram showing changes in the turbidity of the LAMP reaction solution at the wavelength of 500 nm over time.

The LAMP reaction was conducted in a quartz cell (1 cm cell) at 65° C. for 1.5 hour. The composition of the reaction solution and materials such as primers are the same as those used in Example 1. During the reaction, the absorbance at 500 nm was measured over time. As a result, the negative control did not exhibit any change in the absorbance, however, the positive control exhibited an increase in the absorbance having a peak at 60 minutes (FIG. 7). In FIG. 7, the symbol "○" represents a reaction solution and the symbol "●" represents a negative control (without template).

Similarly, the LAMP reaction was conducted in a quarts cell at 65° C. for 40 minutes using $1 \times 10^{-20}$ mol prostate-specific antigen (PSA) DNA (SEQ ID NO: 6) as a template, and the absorbance at A 400 nm was measured over time.

(SEQ ID NO: 6)
5'-TGCTTGTGGCCTCTCGTGGCAGGGCAGTCTGCGGCGGTGTTCTGGTG

CACCCCCAGTGGGTCCTCACAGCTGCCCACTGCATCAGGAACAAAAGCGT

GATCTTGCTGGGTCGGCACAGCCTGTTTCATCCTGAAGACACAGGCCAGG

TATTTCAGGTCAGCCACAGCTTCACACACCC-3'

In SEQ ID NO: 6, regions corresponding to a target region, F1c, F2c, F3c, R1, R2, and R3 are as follows.

Target region: Positions 91 to 102 in the nucleotide sequence shown in SEQ ID NO: 6 (12 bp)

F1c: Positions 68 to 90 in the nucleotide sequence shown in SEQ ID NO: 6 (23 bp)

F2c: Positions 26 to 44 in the nucleotide sequence shown in SEQ ID NO: 6 (19 bp)

F3c: Positions 1 to 18 in the nucleotide sequence shown in SEQ ID NO: 6 (18 bp)

R1: Positions 103 to 122 in the nucleotide sequence shown in SEQ ID NO: 6 (22 bp)

R2: Positions 139 to 161 in the nucleotide sequence shown in SEQ ID NO: 6 (23 bp)

R3: Positions 162 to 178 in the nucleotide sequence shown in SEQ ID NO: 6 (17 bp)

Primers having the following sequences were put into the reaction solution and allowed to react at 65° C. for 1 hour.

Primers:

1600 nM inner primer FA
(SEQ ID NO: 7)
5'-TGTTCCTGATGCAGTGGGCAGCTTTAGTCTGCGGCGGTGTTCTG-3'

1600 nM inner primer RA
(SEQ ID NO: 8)
5'-TGCTGGGTCGGCACAGCCTGAAGCTGACCTGAAATACCTGGCCT
G-3'

400 nM outer primer F3
(SEQ ID NO: 9)
5'-TGCTTGTGGCCTCTCGTG-3'

400 nM outer primer R3
(SEQ ID NO: 10)
5'-GGGTGTGTGAAGCTGTG-3'

Figure 8:
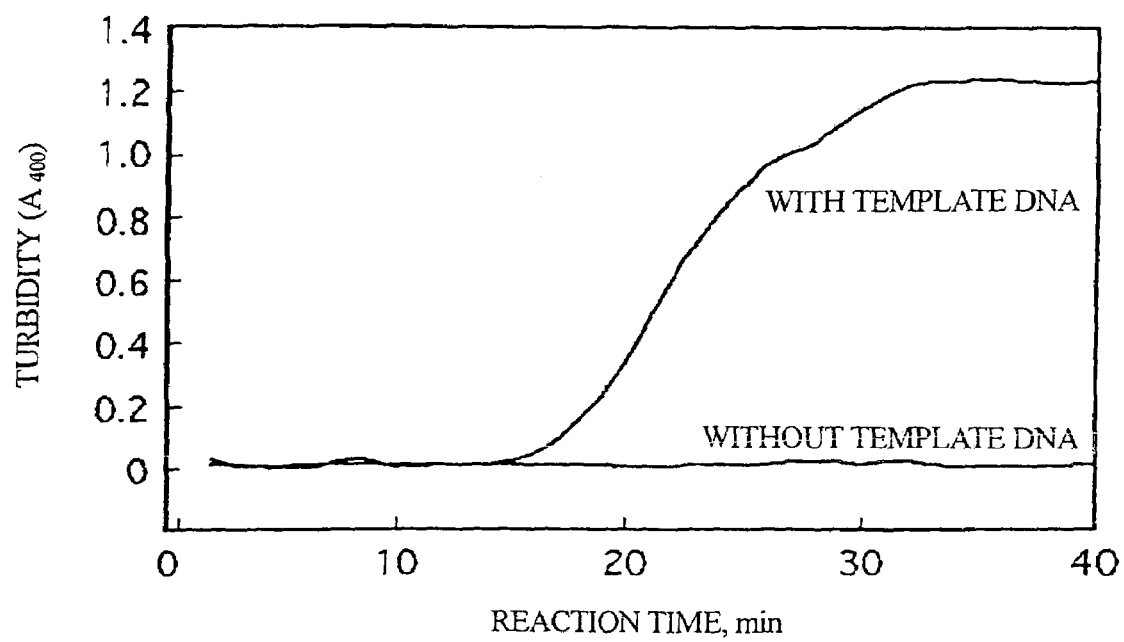
FIG. 8 is a diagram showing changes in the turbidity of the LAMP reaction solution at the wavelength of 400 nm over time.

As a result, the negative control did not exhibit any change in absorbance, however the positive control reached a plateau in about 30 minutes (FIG. 8).

This result demonstrates that observation of the white precipitate of magnesium pyrophosphate over time enabled the monitoring of nucleic acid amplification by the LAMP method over time.

EXAMPLE 5

Correlation Between Turbidity and Amount of DNA Synthesized

Figure 9:
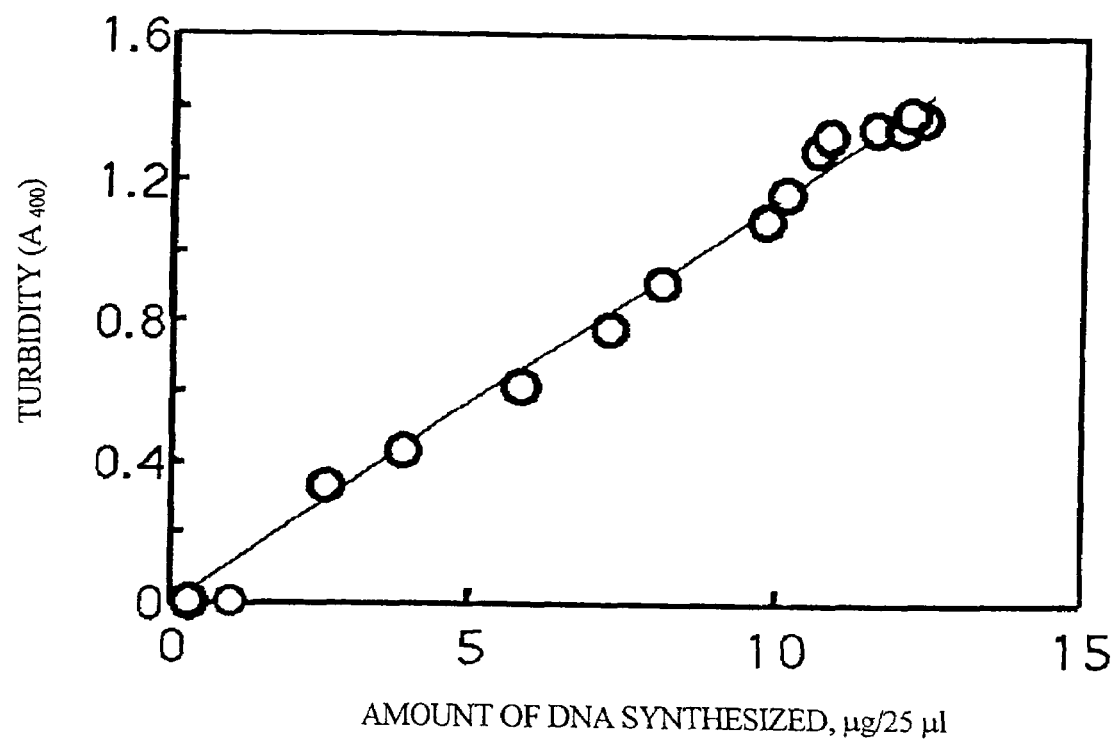
FIG. 9 is a diagram showing a correlation between the turbidity and the amount of DNA synthesized.

The LAMP reaction was carried out using PSA DNA as a template in the same manner as Example 4. Turbidity was measured (A 400 nm) and DNA was quantified over time. DNA was quantified using PicoGreen dsDNA quantifying kit (manufactured by Molecular Probe). The correlation between the turbidity and the amount of DNA is shown in FIG. 9. As is apparent from FIG. 9, a linear correlation can be observed between the turbidity and the amount of DNA, and it was exhibited that the turbidity increased in proportion to the amount of DNA synthesized.

EXAMPLE 6

Figure 10:
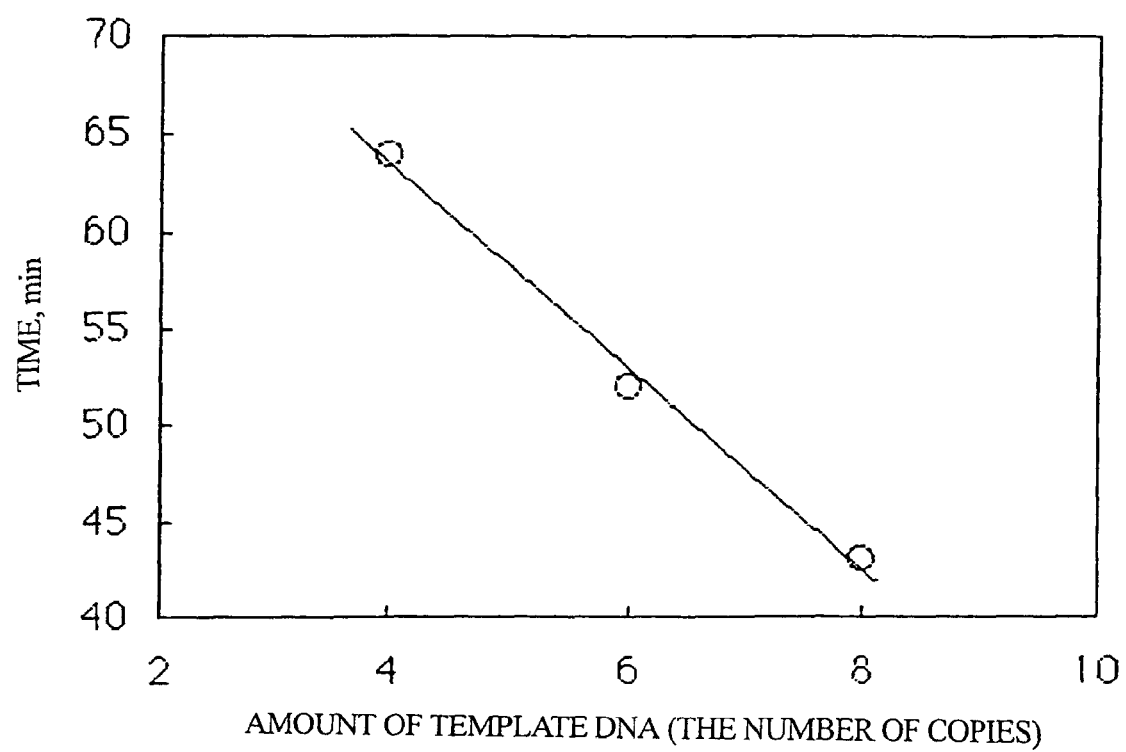
FIG. 10 is a diagram showing a correlation between the threshold time and the amount of template DNA.

Quantification of Template DNA by LAMP Reaction $10^4$, $10^6$, and $10^8$ molecules of PSA DNA were used as templates, and the turbidity (A 400 nm) was measured in real time, and the time for the turbidity to reach 1.0 (threshold time) was measured. The correlation between the amount of DNA and the threshold time was shown in FIG. 10. As is apparent from FIG. 10, a linear correlation was observed between the amount of DNA and the threshold time. Thus, it was demonstrated that the amount of the template DNA could be quantified by measuring the turbidity in real time and determining the threshold time.

EXAMPLE 7

Precipitation Using Coagulant

400 μM of polyacrylic acid (MW 100,000) or 10 mM carboxymethyldextran (MW 10,000) was added to the LAMP reaction solution as a coagulant, and the LAMP reaction was carried out. As a result, the amount of the precipitate increased with the addition of a coagulant.

EXAMPLE 8

Coloring of Insoluble Substance

Whether coloring the white precipitate of magnesium pyrophosphate would facilitate the detection or not was examined. 750 μl of Acid Orange was added for 0.1 g of magnesium pyrophosphate (final concentration of 65 μM). As a control, a solution of Acid Orange only was prepared. After stirring at room temperature for 4 hours, the absorbance of the supernatant for Acid Orange was measured, and the amount coloring onto magnesium pyrophosphate was calculated based on differences from the absorbance of the control solution.

As a result, 52.8 nmol of Acid Orange was used to coloring onto 0.1 g magnesium pyrophosphate. This indicates that about one half of Acid Orange added to the reaction system was adsorbed onto the white precipitate of magnesium pyrophosphate. This result suggested that detection could be facilitated by adsorption of the dye onto the white precipitate of magnesium pyrophosphate. Also, detection using changes in color of the supernatant as an indicator was possible.

Free Text of Sequence Listing
  SEQ ID NO: 1; Synthetic DNA
  SEQ ID NO: 2; Synthetic DNA
  SEQ ID NO: 3; Synthetic DNA
  SEQ ID NO: 4; Synthetic DNA
  SEQ ID NO: 5; Synthetic DNA
  SEQ ID NO: 6; Synthetic DNA
  SEQ ID NO: 7; Synthetic DNA
  SEQ ID NO: 8; Synthetic DNA
  SEQ ID NO: 9; Synthetic DNA
  SEQ ID NO: 10; Synthetic DNA

INDUSTRIAL APPLICABILITY

The present invention provides a novel method for detecting the occurrence of nucleic acid amplification. According to the method of the present invention, an insoluble substance generated by the amplification can be detected by the occurrence of turbidity or precipitation. Thus, the occurrence of amplification can be detected in a very simple manner.

---

The invention claimed is:

1. A kit for detecting the occurrence of nucleic acid amplification or for monitoring nucleic acid amplification comprising the following elements:
(a) when a first arbitrary sequence F1c, a second arbitrary sequence F2c, and a third arbitrary sequence F3c are selected in that order from the 3' terminus in a target region toward the 3' terminus on the polynucleotide chain, and a fourth arbitrary sequence R1, a fifth arbitrary sequence R2, and a sixth arbitrary sequence R3 are selected in that order from the 5' terminus in the target region toward the 5' terminus of the nucleotide chain,
a primer containing sequence F2 which is complementary to F2c and, on the 5' side of F2, the same sequence as F1c;
a primer containing sequence F3 which is complementary to F3c;
a primer containing the same sequence as R2 and, on the 5' side of the sequence, sequence R1c which is complementary to R1; and
a primer containing the same sequence as R3;
(b) a polymerase catalyzing strand displacement-type synthesis of complementary chain;
(c) a nucleotide serving as a substrate for the element (b);
(d) a melting temperature regulator; and
(e) a coagulant.

2. A kit for detecting the occurrence of nucleic acid amplification or for monitoring nucleic acid amplification comprising the following elements:
(a) when a first arbitrary sequence F1c and a second arbitrary sequence F2c are selected in that order from the 3' terminus in a target region toward the 3' terminus on the polynucleotide chain and a third arbitrary sequence R1 and a fourth arbitrary sequence R2 are selected in that order from the 5' terminus in the target region toward the 5' terminus of the nucleotide chain,
a primer containing sequence F2 which is complementary to F2c and, on the 5' side of F2, the same sequence as F1c; and
a primer containing the same sequence as R2 and, on the 5' side of the sequence, sequence R1c which is complementary to R1;
(b) a polymerase catalyzing strand displacement-type synthesis of complementary chain;
(c) a nucleotide serving as a substrate for the element (b);
(d) a melting temperature regulator; and
(e) a coagulant.

3. The kit according to claim 1, wherein the melting temperature regulator is any of betaine, trimethylamine N-oxide, proline, dimethylsulfoxide, or formamide, and the coagulant is polyacrylic acid or carboxymethyldextran.

4. The kit according to claim 2, wherein the melting temperature regulator is any of betaine, trimethylamine N-oxide, proline, dimethylsulfoxide, or formamide, and the coagulant is polyacrylic acid or carboxymethyldextran.

5. The kit according to claim 1, wherein the polymerase is selected from group consisting of Bst DNA polymerase, Bca (exo-) DNA polymerase, the Klenow fragment of E. coli DNA polymerase I, Vent DNA polymerase, Vent(Exo-) DNA polymerase, DeepVent DNA polymerase, DeepVent(Exo-) DNA polymerase, φ29 phage DNA polymerase, MS-2 phage DNA polymerase, Z-Taq DNA polymerase, and KOD DNA polymerase.

6. The kit according to claim 2, wherein the polymerase is selected from group consisting of Bst DNA polymerase, Bca (exo-) DNA polymerase, the Klenow fragment of E. coli DNA polymerase I, Vent DNA polymerase, Vent(Exo-) DNA polymerase, DeepVent DNA polymerase, DeepVent(Exo-) DNA polymerase, φ29 phage DNA polymerase, MS-2 phage DNA polymerase, Z-Taq DNA polymerase, and KOD DNA polymerase.

* * * * *

UNITED STATES PATENT AND TRADEMARK OFFICE
CERTIFICATE OF CORRECTION

PATENT NO. : 7,745,135 B2  Page 1 of 1
APPLICATION NO. : 12/107001
DATED : June 29, 2010
INVENTOR(S) : Yasuyoshi Mori It is certified that error appears in the above-identified patent and that said Letters Patent is hereby corrected as shown below:

Title Page, Item (73) Assignee,
Please correct name of Assignee from "Eiken Kagaku Kabushiki Kaisya" to
--Eiken Kagaku Kabushiki Kaisha--.

Signed and Sealed this

Seventeenth Day of August, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 172
<212> TYPE: DNA
<213> ORGANISM: Artificial Sequence
<220> FEATURE:
<223> OTHER INFORMATION: synthetically generated oligonucleotide

<400> SEQUENCE: 1
gcttatcttt ccctttattt ttgctgcggt aagtcgcata aaaaccattc ttcataattc        60
aatccattta ctatgttatg ttctgagggg agtgaaaatt cccctaattc gatgaagatt       120
cttgctcaat tgttatcagc tatgcgccga ccagaacacc ttgccgatca gc               172
```

```
<210> SEQ ID NO 2
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 2
tcccctcaga acataacata gtaatgcggt aagtcgcata aaaaccattc                    50

<210> SEQ ID NO 3
<211> LENGTH: 47
<212> TYPE: DNA
<213> ORGANISM: Artificial Sequence
<220> FEATURE:
<223> OTHER INFORMATION: synthetically generated oligonucleotide

<400> SEQUENCE: 3
tgaaaattcc cctaattcga tgaggtcggc gcatagctga taacaat                      47

<210> SEQ ID NO 4
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 4
gcttatcttt ccctttattt ttgc                                               24

<210> SEQ ID NO 5
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 5
gctgatcggc aaggtgttct                                                    20

<210> SEQ ID NO 6
<211> LENGTH: 178
<212> TYPE: DNA
<213> ORGANISM: Artificial Sequence
<220> FEATURE:
<223> OTHER INFORMATION: synthetically generated oligonucleotide

<400> SEQUENCE: 6
tgcttgtggc ctctcgtggc agggcagtct gcggcggtgt tctggtgcac ccccagtggg        60
tcctcacagc tgcccactgc atcaggaaca aaagcgtgat cttgctgggt cggcacagcc       120
tgtttcatcc tgaagacaca ggccaggtat ttcaggtcag ccacagcttc acacacc          178

<210> SEQ ID NO 7
<211> LENGTH: 44
<212> TYPE: DNA
<213> ORGANISM: Artificial Sequence
<220> FEATURE:
<223> OTHER INFORMATION: synthetically generated oligonucleotide

<400> SEQUENCE: 7
tgttcctgat gcagtgggca gctttagtct gcggcggtgt tctg                         44

<210> SEQ ID NO 8
<211> LENGTH: 45
<212> TYPE: DNA
```

-continued

```
<213> ORGANISM: Artificial Sequence
<220> FEATURE:
<223> OTHER INFORMATION: synthetically generated oligonucleotide

<400> SEQUENCE: 8
tgctgggtcg gcacagcctg aagctgacct gaaatacctg gcctg                45

<210> SEQ ID NO 9
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 9
tgcttgtggc ctctcgtg                                              18

<210> SEQ ID NO 10
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 10
gggtgtgtga agctgtg                                               17
```